United States Patent
Knight et al.

(10) Patent No.: US 7,282,720 B2
(45) Date of Patent: Oct. 16, 2007

(54) RADIATION SENSOR DEVICE AND RADIATION SOURCE MODULE CONTAINING SAME

(75) Inventors: Douglas Gordon Knight, London (CA); Alex M. W. Verdun, London (CA)

(73) Assignee: Trojan Technologies Inc. (CA)

( * ) Notice: Subject to any disclaimer, the term of this patent is extended or adjusted under 35 U.S.C. 154(b) by 0 days.

(21) Appl. No.: 10/952,479

(22) Filed: Sep. 29, 2004

(65) Prior Publication Data
US 2005/0098736 A1   May 12, 2005

Related U.S. Application Data

(60) Provisional application No. 60/506,144, filed on Sep. 29, 2003.

(51) Int. Cl.
*G01J 1/42* (2006.01)
(52) U.S. Cl. ...................................... 250/372
(58) Field of Classification Search ............... 250/372, 250/432
See application file for complete search history.

(56) References Cited

U.S. PATENT DOCUMENTS

| | | | |
|---|---|---|---|
| 4,017,734 A | 4/1977 | Ross | |
| 5,093,576 A * | 3/1992 | Edmond et al. | 250/370.01 |
| 5,514,871 A | 5/1996 | Hayes et al. | |
| 5,539,210 A * | 7/1996 | Maarschalkerweerd | 250/372 |
| 6,057,917 A | 5/2000 | Petersen et al. | |
| 6,611,375 B2 * | 8/2003 | Knapp | 359/361 |
| 2005/0063045 A1 * | 3/2005 | Sakakibara et al. | 359/361 |

OTHER PUBLICATIONS

Canfield et al., "Absolute silicon photodiodes for 160 nm to 254 nm photons", Metrologia, 1998, 35, pp. 329-334.

* cited by examiner

*Primary Examiner*—David Porta
*Assistant Examiner*—Marcus H Taningco
(74) *Attorney, Agent, or Firm*—Katten Muchin Rosenman LLP (57) ABSTRACT

A radiation sensor device comprising a body portion having an entrance through which radiation may enter the body portion, a radiation detector and an optical filter interposed between the entrance and the radiation detector. The radiation detector is capable of detecting radiation having at least one wavelength in the range of from about 125 nm to about 1100 nm, and comprises: (i) a silicon-containing material comprising an n-doped layer disposed on a pair of p-doped layers, and (ii) a passivation layer disposed on a radiation impingement surface of the silicon-containing material, the passivation layer comprising nitrided silicon dioxide, a metal silicide and mixtures thereof. The optical filter has: (i) an optical transmittance of at least about 40% at a wavelength in the range of from about 175 nm to about 300 nm, and (ii) an optical transmittance of no greater than about 5% at a wavelength greater than about 350 nm.

39 Claims, 4 Drawing Sheets

RADIATION SENSOR DEVICE AND RADIATION SOURCE MODULE CONTAINING SAME

CROSS-REFERENCE TO RELATED APPLICATION

The present application claims the benefit under 35 U.S.C. §119(e) of provisional patent application Ser. No. 60/506,144, filed Sep. 29, 2003, the contents of which are hereby incorporated by reference.

BACKGROUND OF THE INVENTION

1. Field of the Invention

In one of its aspects, the present invention relates to a radiation source assembly. In another of its aspects, the present invention relates to a radiation source module comprising a novel radiation source assembly having incorporated therein an optical radiation sensor.

2. Description of the Prior Art

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of microwatt seconds per square centimeter). Ultraviolet water disinfection units such as those commercially available from Trojan Technologies Inc. under the tradenames Trojan UV MaX™, Trojan UV Logic™ and Trojan UV Swift™, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the tradenames UV3000™, UV3000 Plus™ and UV4000™, employ the same principle to disinfect waste water. Generally, the practical applications of these treatment systems relates to submersion of a treatment module or system in an open channel wherein the wastewater is exposed to radiation as it flows past the lamps. For further discussion of fluid disinfection systems employing ultraviolet radiation, see any one of the following:

U.S. Pat. No. 4,482,809,
U.S. Pat. No. 4,872,980,
U.S. Pat. No. 5,006,244,
U.S. Pat. No. 5,418,370,
U.S. Pat. No. 5,539,210, and
U.S. Pat. No. Re36,896.

Most commercially available ultraviolet radiation fluid treatment systems employ so-called low pressure (including low pressure/high output) lamps (e.g., such systems available from Trojan Technologies Inc. under the trade-names UV3000™ and UV3000 Plus™) or medium pressure lamps (e.g., such systems available from Trojan Technologies Inc. under the trade-name UV4000™).

In many applications, it is desirable to monitor the level of ultraviolet radiation present within the water under treatment. In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingement of the particular radiation wavelength or range of radiation wavelengths of interest by producing a repeatable signal level (in volts or amperes) on output leads.

Conventional passive sensor devices (e.g., photodiodes, photoresistors and the like) used to monitor ultraviolet radiation levels are responsive to light according to the light absorbing properties of the active material in the sensor. For example, silicon-based detectors commonly used in light detection are responsive to light over the range of from about 125 nm to about 1100 nm. This range of sensitivity encompasses many types of radiation and is much larger than needed to detect radiation in the ultraviolet region—i.e., radiation having at least one wavelength in the range of less that about 300 nm, ideally from about 240 nm to about 290 nm for disinfection and/or from about 175 to about 300 nm for treatment of chemical contaminants. The term "treatment of contaminants" is intended to mean reduction of the concentration of one or more contaminants in the water —in some cases, it can result in complete removal of the contaminant.

The use of such conventional passive sensor devices can result in inaccurate irradiance values in a disinfection system if a broad range of radiation is present in the disinfection system—i.e., radiation falling broadly in the range of from about 290 nm to about 1100 nm. Conventional silicon-based sensors also suffer from degradation in performance when exposed to the high intensity ultraviolet radiation used for prolonged periods of time in fluid treatment and/or disinfection systems.

A relatively recent development in the art of ultraviolet radiation fluid treatment systems is the use of a silicon carbide (SiC) detector as a sensing device. The relatively large bandgap of SiC narrows the wavelength range over which the detector is sensitive—i.e., to a wavelength range of from about 220 nm to about 400 nm. Thus, the SiC detector is relatively insensitive to radiation having at least one wavelength greater than about 400 nm. In turn, this can reduce the likelihood that the above-mentioned measurement error will occur. More information on this application of SiC detectors may be found in U.S. Pat. No. 6,057,917 [Petersen et al.] and U.S. patent application publication 2002/162,970 [Sasges].

An emerging application of fluid treatment systems which utilize medium pressure mercury lamps is the removal of chemical contaminants and dissolved organic carbon in water. Ultraviolet radiation having a wavelength in the range of from about 175 nn to about 300 nm is suitable for this application, where the exact wavelength range depends on the specific application. Unfortunately, silicon carbide is only responsive to radiation having a wavelength of greater than about 220 nm and thus a sensor device using SiC is not well suited for monitoring UV light intensity in the lower wavelength range for applications such as chemical contamination removal.

U.S. Pat. No. 6,611,375 [Knapp] teaches selectively tuned ultraviolet optical filters and methods of use thereof. More specifically, Knapp teaches optical filters that purportedly are tuned specifically for ultraviolet water purification, and, as such, these optical filters are said to be characterized by: (i) transmitting effectively within the wavelengths that contribute to ultraviolet sterilization (centered at 254 nm); (ii)

selectively rejecting those background discrete wavelengths in the UV/VIS/IR emission spectra of typical mercury lamps and which fall within the sensitivity region of photodiodes; and (iii) are resistant to damage from high intensity ultraviolet radiation. More, particularly, Knapp teaches optical filters having: (i) an optical transmittance of at least about 40%, more preferably at least about 70%, still more preferably at least about 75% or 79% at a wavelength of about 254 nm, and (ii) an optical transmittance of no greater than 5% at wavelengths of 313 nm to 580 nm and 1000 nm to 1140 nm. The profile of a sensor device employing such an optical filter is illustrated in FIG. 11 of Knapp—this Figure illustrates that the optical filter of Knapp allows radiation having a wavelength in the range of from about 600 nm to about 950 nm to pass therethrough. Unfortunately, even radiation having a wavelength in the range of from about 600 nm to about 950 nm can result in inaccurate irradiance values for conventional silicon-based photodiodes—this issue is not addressed or otherwise dealt with in the teachings of Knapp.

Thus, despite the advances made in the art, there is room for improvement. Specifically, it would be desirable to have a radiation sensor device (particularly for use in ultraviolet radiation fluid treatment systems) capable of detecting and responding to radiation having at least one wavelength in the range of from about 175 nm to about 350 nm while avoiding the disadvantages of the prior art.

SUMMARY OF THE INVENTION

It is an object of the present invention to obviate or mitigate at least one of the above-mentioned disadvantages of the prior art.

It is an object of the present invention to provide a novel radiation sensor device which obviates or mitigates at least one of the above-mentioned disadvantages of the prior art.

It is another object of the present invention to provide a novel radiation source module which obviates or mitigates at least one of the above-mentioned disadvantages of the prior art.

It is yet another object of the present invention to provide a novel fluid treatment system which obviates or mitigates at least one of the above-mentioned disadvantages of the prior art.

Accordingly, in one of its aspects, the present invention provides a radiation sensor device comprising:

a body portion having an entrance through which radiation may enter the body portion;

a radiation detector capable of detecting radiation having at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon-containing material, the passivation layer comprising nitrided silicon dioxide, a metal silicide and mixtures thereof; and an optical filter interposed between the entrance and the radiation detector, the optical filter having: (i) an optical transmittance of at least about 40% at a wavelength in the range of from about 175 nm to about 300 nm, and (ii) an optical transmittance of no greater than 5% at a wavelength greater than about 350 nm.

In another of its aspects, the present invention provides a radiation source module comprising a frame comprising a first support member and a radiation source assembly connected to the first support member, the radiation source assembly comprising an radiation source and the frame further comprising a radiation sensor device comprising a body portion having an entrance through which radiation may enter the body portion;

a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at wavelengths greater than about 350 nm.

In yet another of its aspects, the present invention provides a fluid treatment system comprising a fluid treatment zone in which is disposed a radiation sensor device comprising:

a body portion having an entrance through which radiation may enter the body portion;

radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and an optical filter interposed between the entrance and the radiation detector, the optical filter having: (i) an optical transmittance of at least about 40% at a wavelength in the range of from about 175 nm to about 300 nm, and (ii) an optical transmittance of no greater than 5% at wavelengths greater than about 350 nm.

Thus, the present inventors have discovered a novel radiation sensor device which combines a particular optical filter with a particular radiation detector. The combination of these elements, as set out herein, provides a radiation sensor device (particularly for use in ultraviolet radiation fluid treatment systems) that is capable of detecting and responding to radiation at a wavelength in the range of from about 175 nm to about 300 nm. The present radiation sensor device is also advantageous since it provides such sensitivity while, at the same time, obviating or mitigating damage to the radiation detector or sensing element in the device by incorporating a robust silicon-based detector which is resistant to damage by light in the transmission range of the optical filter. The optical filter is resistant to damage from all light blocked by the filter. This results in a novel radiation sensor device resistant to high intensity ultraviolet light. Further, the present radiation sensor device may obviate or mitigate the need for using silicon carbide based radiation detectors or photodiodes as the sensing element in the device. This allows for the possibility of using lower cost radiation detector or sensing elements in the present device, and allows sensing of short wavelength ultraviolet light below about 200 nm.

BRIEF DESCRIPTION OF THE DRAWINGS

Embodiments of the present invention will be described with reference to the accompanying drawings, wherein like numerals designate like elements, and in which.

DETAILED DESCRIPTION OF THE PREFERRED EMBODIMENTS

A first element of the present radiation sensor device is an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at a wavelength of greater than about 350 nm.

A suitable optical filter for use in the present radiation sensor device is described in Knapp referred to above.

Preferably, the optical filter has an optical transmittance of at least about 70% at a wavelength in the range of from about 175 nm to about 300 nm. More preferably, the optical filter has an optical transmittance of at least about 80% at a wavelength in the range of from about 175 nm to about 300 nm.

Preferably, the optical filter has an optical transmittance of no greater than about 5% at a wavelength in the range of from about 350 to about 1140 nm. More preferably, the optical filter has an optical transmittance of no greater than about 5% at a wavelength in the range of from about 350 to about 580 nm. More preferably, the optical filter has an optical transmittance of no greater than about 5% at a wavelength in the range of from about 1000 nm to about 1140 nm. Even more preferably, the optical filter has an optical transmittance of no greater than about 5% at a wavelength in the range of from about 350 to about 580 nm and in the range of from about 1000 nm to about 1140 nm. Even more preferably, the optical filter has an optical transmittance of no greater than about 1% at a wavelength in the range of from about 350 to about 580 nm and in the range of from about 1000 nm to about 1140 nm. Even more preferably, the optical filter has an optical transmittance of no greater than about 2% at one or more of the following wavelengths: 313 nm, 365 nm, 405 nm, 436 nm 546 nm, 579 nm and 1015 nm. Most preferably, the optical filter has an optical transmittance of no greater than about 2% at each of the following wavelengths: 313 nm, 365 nm, 405 nm, 436 nm 546 nm, 579 nm and 1015 nm.

Preferably, the optical filter further comprises a supplementary filter, which blocks radiation having a wavelength in the range of from about 600 to about 950 nm. The provision of such a supplementary filter is particularly useful when the radiation being sensed emanates from a medium pressure ultraviolet radiation lamp or source. If present it is preferred that the supplementary filter has an optical transmittance of no greater than about 5%, more preferably no greater than about 1%, most preferably no greater than about 0.1%, at a wavelength in the range of from about 600 nm to about 950 nm.

Preferably, the optical filter comprises a substrate and a coating (or coatings) having the prescribed transmittance properties. Non-limiting examples of suitable substrate materials may be selected from the group comprising glass, plastic, fused silica, sapphire and metal. In one preferred embodiment, the substrate comprises fused silica. In another preferred embodiment, the substrate comprises ultraviolet radiation transparent glass.

The coating may present as one or more layers. Preferably, the coating comprising a plurality of layers.

Preferably, the coating comprises one or more of $SiO_2$, $Al_2O_3$, SiO, fluorides such as barium fluoride and lanthanum fluoride, MgO, $TiO_2$, $ZrO_2$, $Ta_2O_5$, $HfO_2$ and mixtures thereof.

Thus, in the event that radiation have at least one wavelength in the range of from about 600 to about 950 nm impinges on the sensor device, a supplementary filter element which blocks radiation in this wavelength range can be employed. Such an additional filter element can comprise an additional series of coatings similar to those employed by Knapp and described above, or a more conventional filter such as a metal-dielectric-metal UV bandpass filter. This additional filter element could advantageously be placed between the first filter element and the radiation detector, recognizing that some of the ultraviolet radiation has already been filtered by the radiation resistant first filter element and therefore does not impinge on the additional filter element. Alternatively, this additional filter element could disposed above the first filter element or incorporated in the first filter element.

A second element of the present radiation sensor device is a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide (e.g., a combination of $Si_3N_4$ and $SiO_2$), a metal silicide and mixtures thereof. More information about such a radiation sensor device may be obtained from Canfield et al. in *Metrologia* 35, 1998, pg. 329-334.

Preferably, in the radiation detector, the n-doped layer is thinner than the p-doped layers. More preferably, the radiation detector comprises a p-doped substrate on which is disposed a relatively thin n-doped layer. Most preferably, the radiation detector comprises, in successive layers: a p-doped substrate (bottom), a relatively thin p-doped layer and a relatively thin n-doped layer (top).

In one embodiment of the present radiation sensor device, the optical filter is in the form of a coating (or coatings) having the prescribed transmittance properties and being disposed on a surface of the radiation detector.

Figure 1:
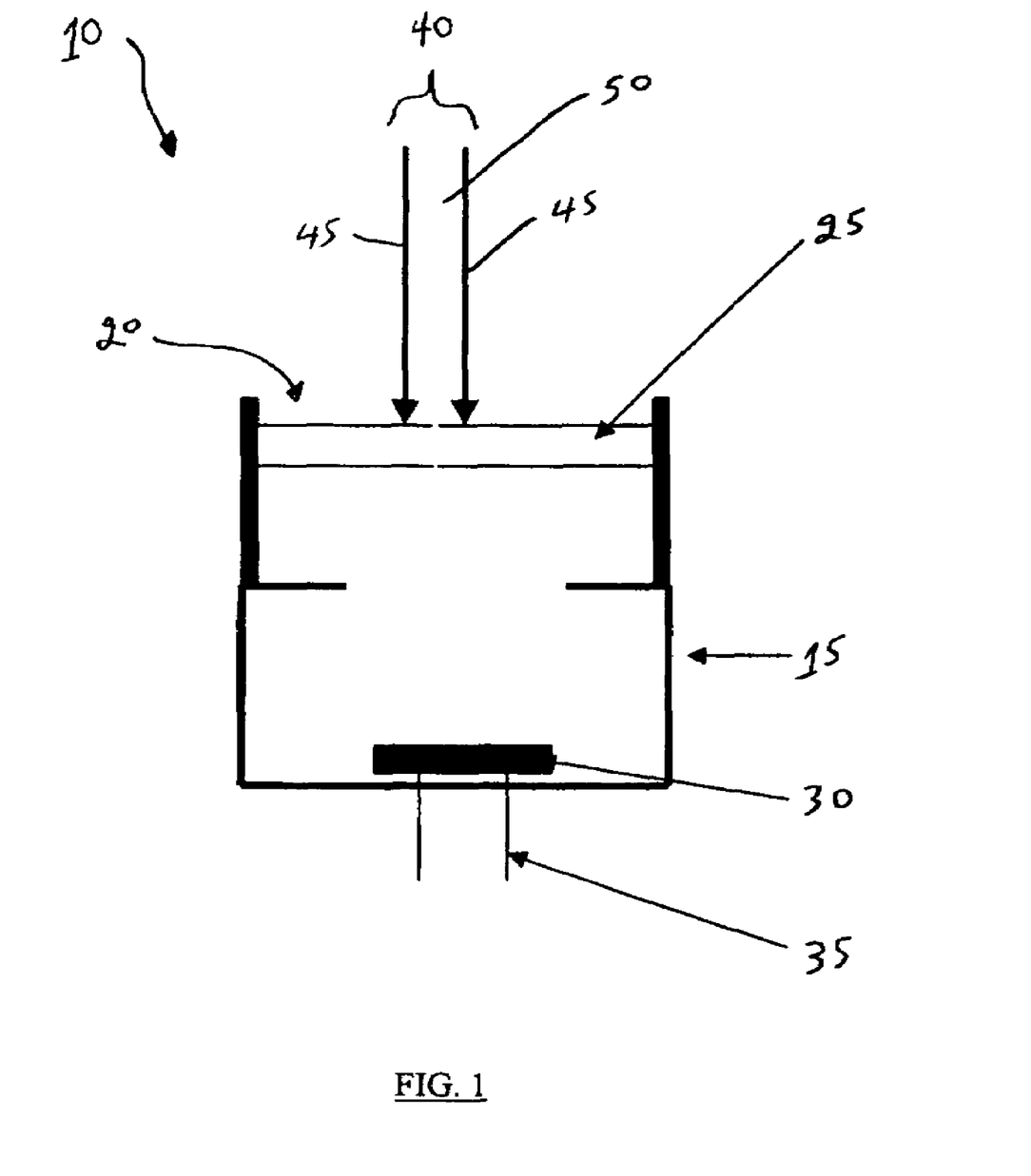
FIG. 1 illustrates a schematic of a radiation sensor device in accordance with the preferred embodiment of the present invention.

With reference to FIG. 1, there is shown a schematic of a radiation sensor device in accordance with the preferred embodiment of the present invention. Radiation sensor device 10 comprises a housing 15 having an entrance 20. Disposed in entrance 20 is an optical filter 25 having the transmittance properties described above. Disposed in housing 15 is a photodiode 30 (or other sensing element) having the properties described above. A pair of electrical connections 35 is connected to photodiode 30.

In operation of radiation sensor device 10, polychromatic radiation 40 passes through entrance 20 and impinges on optical filter 25. Radiation 45 having a wavelength outside the range of from about 100 nm to about 300 nm does not pass through optical filter 25. Radiation 50 having a at least one wavelength in the range of from about 100 nm to about 300 nm (preferably from about 240 to about 300 nm for disinfection and/or from about 175 to about 300 nm for treatment of chemical contaminants) passes through optical filter 25 and impinges on photodiode 30.

Importantly, if an optical filter such as the one described in Knapp is used in the present radiation sensor device, radiation having the wavelength in the range of from about 600 nm to about 950 nm may pass there through as shown in FIG. 11 of Knapp. This problem is obviated or mitigated in the present radiation sensor device owing to the additional optional filter element incorporated into optical filter 25.

As radiation having a wavelength of interest impinges on photodiode 30, it may be detected and a corresponding signal sent to conventional electronics in the art to sense and/or control radiation output.

Figure 2:
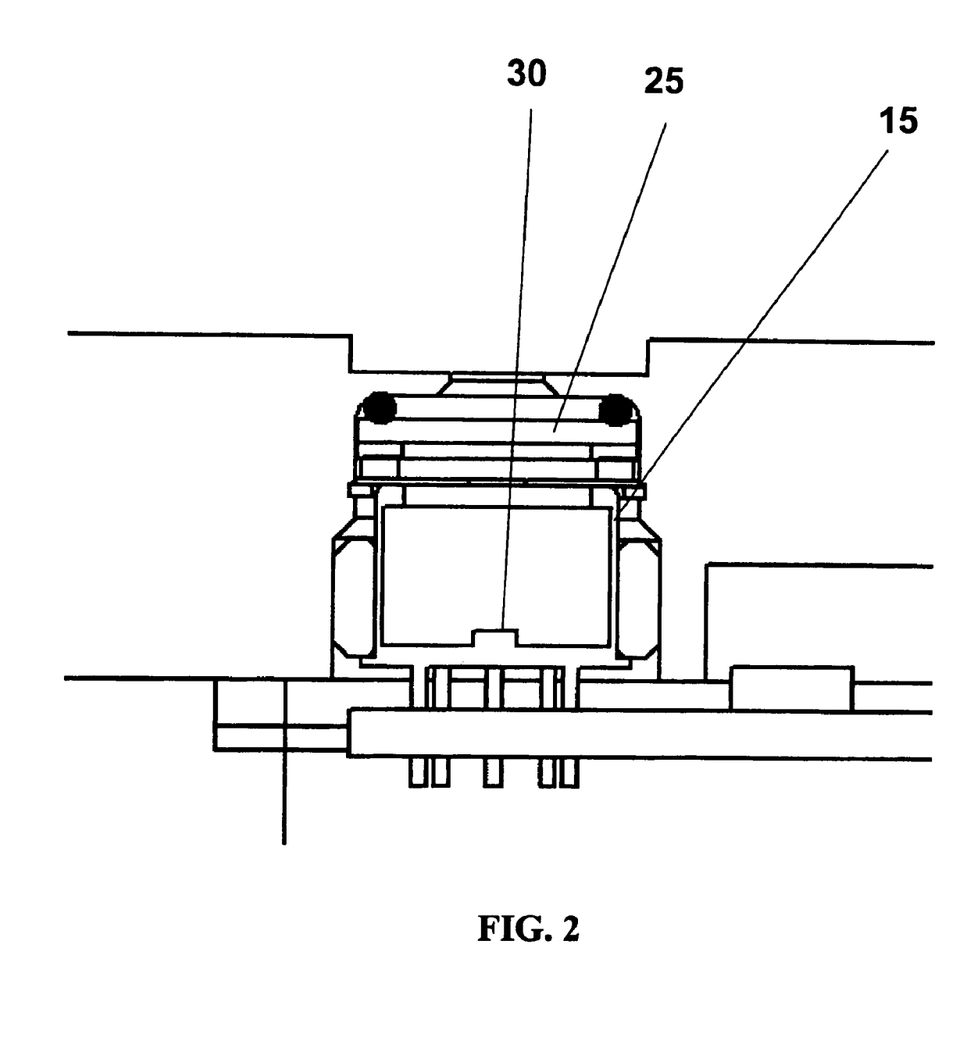
FIG. 2 illustrates a more detailed view of a particular embodiment of the present radiation sensor device.

FIG. 2 provides a more detailed illustration of a particular embodiment of the present radiation sensor device showing placement of the radiation detector and the optical filter in relation to washers, seals and the like conventional art used to construct submersible devices.

The present radiation sensor device may be incorporated in an ultraviolet radiation fluid treatment (e.g., disinfection) system. After sensing radiation, the output of the radiation sensor device may be used to control the ultraviolet radiation sources thereby maintaining irradiance of the ultraviolet radiation in the disinfection wavelength range needed to kill or otherwise inactivate harmful organisms in the fluid being treated. A schematic of a basic disinfection system using the present radiation sensor device is shown in FIG. 3.

Figure 3:
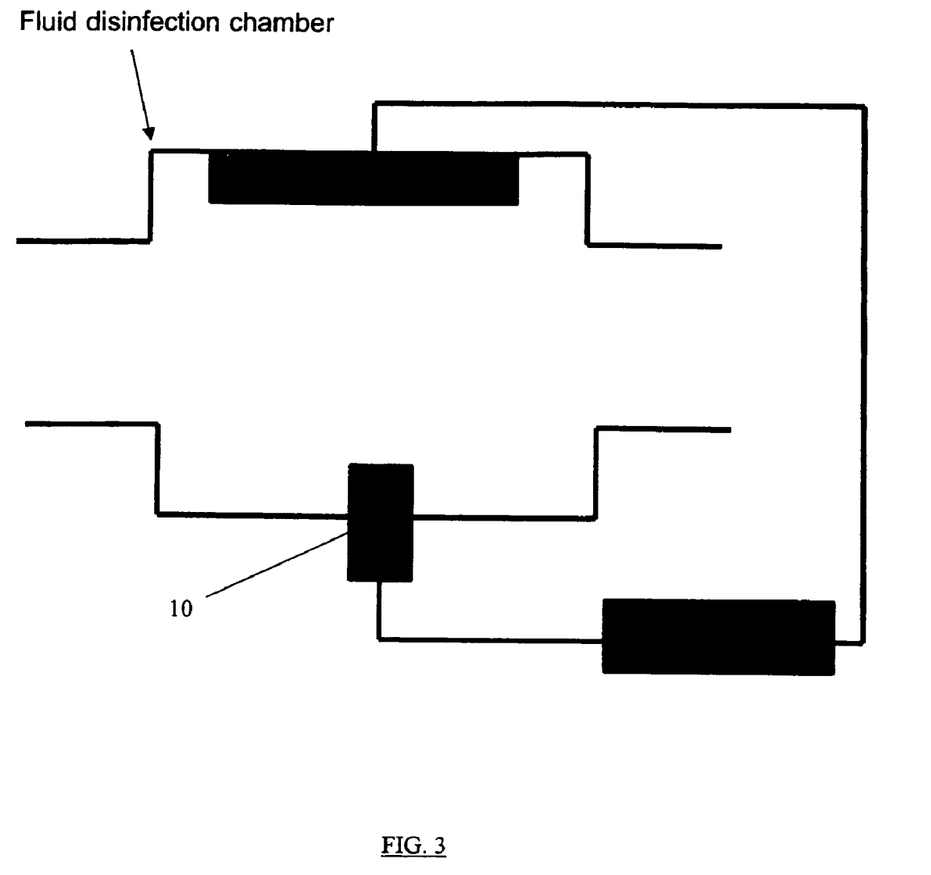
FIG. 3 illustrates a schematic of use of the radiation sensor device of FIG. 1 in a fluid treatment.
Figure 4:
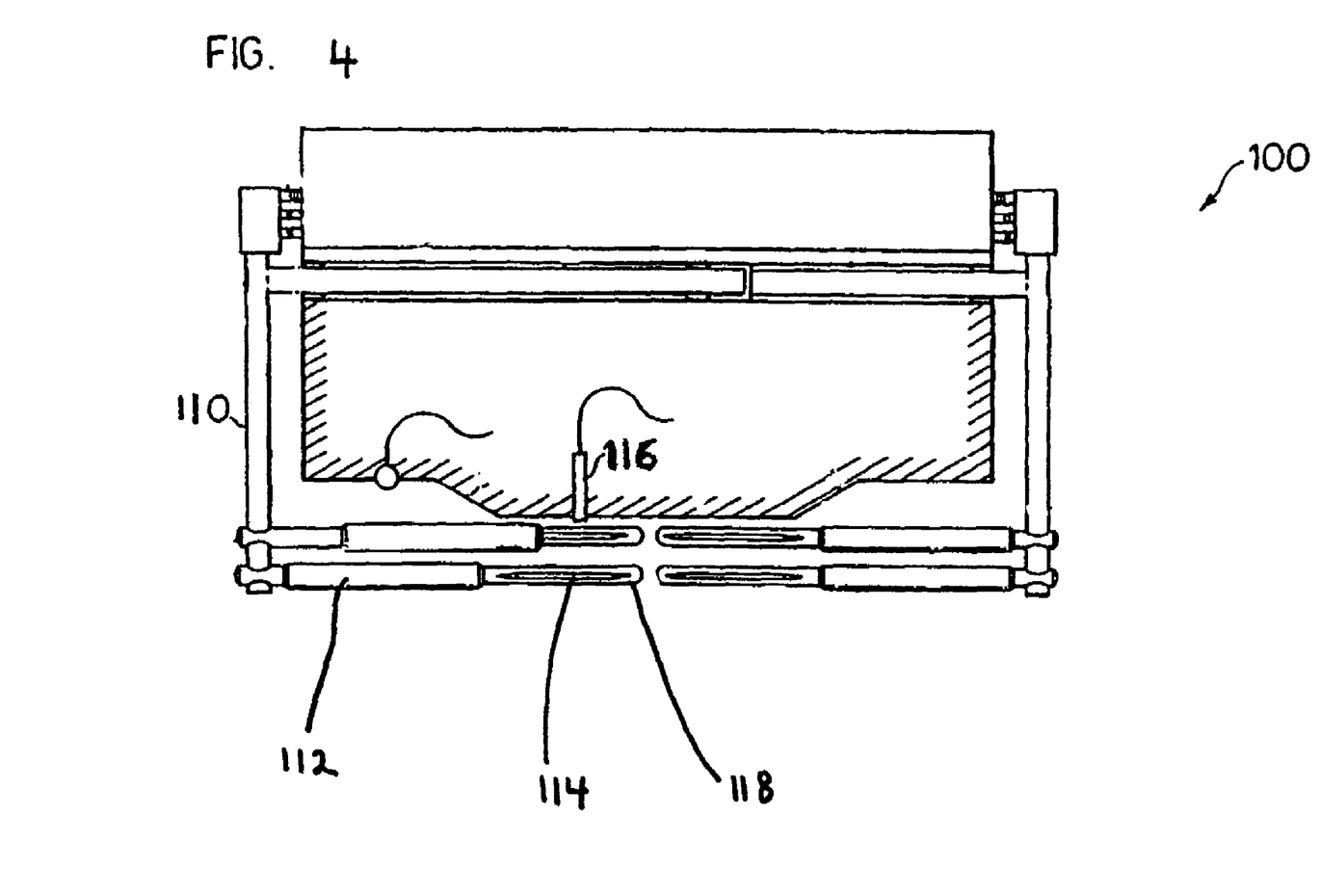
FIG. 4 illustrates a radiation source module in accordance with one embodiment of the present invention.

Thus, with reference to FIG. 3, device 10 detects ultraviolet radiation having at least one wavelength in the range of about 175 nm to about 300 nm emitted by a nearby radiation source. Device 10 then sends signal to the controller which adjusts the power to the ultraviolet light source so that the irradiance of light in the disinfection wavelength range is maintained at a desired level. Fluid passes through the fluid disinfection chamber of the fluid treatment system wherein harmful organisms are killed or otherwise inactivated by the ultraviolet radiation. Similarly, a chemical contamination removal system with a schematic as shown in FIG. 3 can be constructed. The output of the radiation sensor device is used to maintain the irradiance of ultraviolet radiation needed to reduce the concentration of chemical contaminants in the fluid. A radiation source module 100 of the present invention is illustrated in FIG. 4. Radiation source module 100 comprises a frame comprising a first support member 110 and a radiation source assembly 112 connected to first support member 100. Radiation source assembly 112 comprising a radiation source 114 and further comprises a radiation sensor device 116 such as described above. First Support member 100 comprises a hollow passageway (not shown) for receiving a lead wire for conveying electricity radiation source 114. Radiation source assembly 112 further comprises a Quartz sleeve 118 in which is disposed radiation source 114.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation sensor device comprising:
   a body portion having an entrance through which radiation may enter the body portion;
   a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and
   an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at a wavelength of greater than about 350 nm.

2. The radiation sensor device defined in claim 1, wherein the optical filter has an optical transmittance of at least about 70% at a wavelength in the range of from about 175 nm to about 300 nm.

3. The radiation sensor device defined in claim 1, wherein the optical filter has an optical transmittance of at least about 80% at a wavelength in the range of from about 175 nm to about 300 nm.

4. The radiation sensor device defined in claim 1, wherein the optical filter has an optical transmittance of no greater than about 5% at a wavelength in the range of from about 350 to about 1140 nm.

5. The radiation sensor device defined in claim 1, wherein the optical filter has an optical transmittance of no greater than about 5% at a wavelength in the range of from about 350 to about 580 nm.

6. The radiation sensor device defined in claim 1, wherein the optical filter has an optical transmittance of no greater than about 5% at a wavelength in the range of from about 1000 nm to about 1140 nm.

7. The radiation sensor device defined in claim 1, wherein the optical filter has an optical transmittance of no greater than about 5% at a wavelength in the range of from about 350 to about 580 nm and in the range of from about 1000 nm to about 1140 nm.

8. The radiation sensor device defined in claim 1, wherein the optical filter has an optical transmittance of no greater than about 1% at a wavelength in the range of from about 350 to about 580 nm and in the range of from about 1000 nm to about 1140 nm.

9. The radiation sensor device defined in claim 1, wherein the optical filter has an optical transmittance of no greater than about 2% at one or more of the following wavelengths: 313 nm, 365 nm, 405 nm, 436 nm 546 nm, 579 nm and 1015 nm.

10. The radiation sensor device defined in claim 1, wherein the optical filter has an optical transmittance of no greater than about 2% at each of the following wavelengths: 313 nm, 365 nm, 405 nm, 436 nm 546 nm, 579 nm and 1015 nm.

11. The radiation sensor device defined in claim 1, wherein the optical filter comprises a substrate and a coating having the prescribed transmittance properties.

12. The radiation sensor device defined in claim 11, wherein the substrate is selected from the group comprising glass, plastic, fused silica, sapphire and metal.

13. The radiation sensor device defined in claim 11, wherein the substrate comprises fused silica.

14. The radiation sensor device defined in claim 11, wherein the substrate comprises ultraviolet radiation transparent glass.

15. The radiation sensor device defined in claim 11, wherein the coating comprises one or more layers.

16. The radiation sensor device defined in claim 11, wherein the coating comprises $SiO_2$, $Al_2O_3$, SiO, fluorides such as barium fluoride and lanthanum fluoride, MgO, $TiO_2$, $ZrO_2$, $Ta_2O_5$, $HfO_2$ and mixtures thereof.

17. The radiation sensor device defined in claim 11, wherein the optical filter further comprises a supplementary optical filter element having an optical transmittance of no greater than about 5% at a wavelength in the range of from about 600 nm to about 950 nm.

18. The radiation sensor device defined in claim 17, wherein the supplementary optical filter element comprises a coating selected from the group comprising $SiO_2$, $Al_2O_3$, SiO, fluorides such as barium fluoride and lanthanum fluoride, MgO, $TiO_2$, $ZrO_2$, $Ta_2O_5$, $HfO_2$ and mixtures thereof.

19. The radiation sensor device defined in claim 17, wherein the supplementary optical filter element comprises an ultraviolet bandpass filter.

20. The radiation sensor device defined in claim 17, wherein the supplementary optical filter element comprises a metal-dielectric-metal filter.

21. The radiation sensor device defined in claim 11, wherein the optical filter further comprises a supplementary optical filter element having an optical transmittance of no greater than about 1% at a wavelength in the range of from about 600 nm to about 950 nm.

22. The radiation sensor device defined in claim 11, wherein the optical filter further comprises a supplementary optical filter element having an optical transmittance of no greater than about 0.1% at a wavelength in the range of from about 600 nm to about 950 nm.

23. The radiation sensor device defined in claim 1, wherein the optical filter is in the form of a coating having the prescribed transmittance properties and being disposed on a surface of the radiation detector.

24. The radiation sensor device defined in claim 1, wherein the n-doped layer is thinner than at least one of the p-doped layers.

25. The radiation sensor device defined in claim 1, wherein the radiation detector comprises a p-doped substrate on which is disposed a relatively tin n-doped layer.

26. The radiation sensor device defined in claim 1, wherein the radiation detector comprises a p-doped substrate on which is disposed a relatively thin p-doped layer and a relatively thin n-doped layer.

27. A radiation source module comprising a frame comprising a first support member and a radiation source assembly connected to the first support member, the radiation source assembly comprising an radiation source and the frame further comprising a radiation sensor device as defined in claim 1.

28. The radiation source module defined in claim 27, wherein the frame further comprises a second support member opposed to and laterally spaced from the first support member, the at least one radiation source assembly disposed between each of the first support member and the second support member.

29. The radiation source module defined in claim 28, wherein the frame further comprises a third support member interconnecting the first support member and the second support member.

30. The radiation source module defined in claim 27, wherein the frame further comprises a ballast for controlling the at least one radiation source.

31. The radiation source module defined in claim 27, wherein the first support member comprises a hollow passageway for receiving a lead wire for conveying electricity to the at least one radiation source.

32. The radiation source module defined in claim 27, wherein the radiation source module comprises a plurality of radiation source assemblies.

33. The radiation source module defined in claim 27, wherein the radiation source assembly comprises a plurality radiation sources.

34. A fluid treatment system comprising a fluid treatment zone in which is disposed the radiation sensor device defined in claim 1.

35. The fluid treatment system defined in claim 34, wherein the fluid treatment zone comprises a housing through which fluid flows.

36. The fluid treatment system defined in claim 34, wherein the radiation sensor device is secured to the housing.

37. A radiation source module comprising:
(i) a frame comprising a first support member, and a radiation sensor device, the radiation sensor device comprising:
  a body portion having an entrance through which radiation may enter the body portion;
  a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and
  an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at a wavelength of greater than about 350 nm: and
(ii) a radiation source assembly connected to the first support member, the radiation source assembly comprising a radiation source, wherein the radiation source assembly comprises a quartz sleeve in which is disposed the radiation source.

38. A radiation source module comprising:
a frame comprising a first support member; and
a radiation source assembly connected to the first support member, the radiation source assembly comprising:
  a radiation source;
  a quartz sleeve in which is disposed the radiation source; and
  a radiation sensor device disposed in the radiation source assembly, the radiation sensor device comprising:
    a body portion having an entrance through which radiation may enter the body portion;
    a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at a wavelength of greater than about 350 nm, wherein the optical filter comprises a coating disposed on a surface of the quartz sleeve.

39. A radiation source module comprising:

a frame comprising a first support member; and a radiation source assembly connected to the first support member, the radiation source assembly comprising:

a radiation source;

a quartz sleeve in which is disposed the radiation source; and a radiation sensor device disposed in the radiation source assembly, the radiation sensor device comprising:

a body portion having an entrance through which radiation may enter the body portion;

a radiation detector capable of detecting radiation have at least one wavelength in the range of from about 125 nm to about 1100 nm, the radiation detector comprising: (i) a silicon-containing material comprising an n-doped layer disposed on a pair of p-doped layers, and (ii) a passivation layer disposed on a radiation impingement surface of the silicon containing material, the passivation layer comprising nitrided silicon dioxide, a metal silicide and mixtures thereof; and an optical filter interposed between the entrance and the radiation detector, the optical filter having: (i) an optical transmittance of at least about 40% at a wavelength in the range of from about 175 nm to about 300 nm, and (ii) an optical transmittance of no greater than about 5% at a wavelength of greater than about 350 nm, wherein the optical filter comprises a coating disposed on an inner surface of the quartz sleeve.

* * * * *